(12) United States Patent  (10) Patent No.: US 7,942,912 B2
Brockmeyer et al.  (45) Date of Patent: May 17, 2011

(54) OCCIPITOCERVICAL PLATE

(75) Inventors: Douglas L. Brockmeyer, Salt Lake City, UT (US); Nathan Avery, Flagstaff, AZ (US)

(73) Assignee: University of Utah Research Foundation, Salt Lake City, UT (US)

( * ) Notice: Subject to any disclaimer, the term of this patent is extended or adjusted under 35 U.S.C. 154(b) by 1211 days.

(21) Appl. No.: 11/137,036

(22) Filed: May 25, 2005

(65) Prior Publication Data
US 2006/0004363 A1 Jan. 5, 2006

Related U.S. Application Data

(60) Provisional application No. 60/574,282, filed on May 25, 2004.

(51) Int. Cl.
*A61B 17/80* (2006.01)
(52) U.S. Cl. ........................................ 606/280; 606/286
(58) Field of Classification Search .................... 606/70, 606/280–299
See application file for complete search history.

(56) References Cited

U.S. PATENT DOCUMENTS

| | | | |
|---|---|---|---|
| 4,763,644 A | 8/1988 | Webb | |
| 4,805,602 A | 2/1989 | Puno et al. | |
| 4,887,596 A | 12/1989 | Sherman | |
| 4,950,269 A | 8/1990 | Gaines, Jr. | |
| 5,129,388 A | 7/1992 | Vignaud et al. | |
| 5,261,910 A * | 11/1993 | Warden et al. | 606/292 |
| 5,360,429 A | 11/1994 | Jeanson et al. | |
| 5,470,333 A | 11/1995 | Ray | |
| 5,484,439 A * | 1/1996 | Olson et al. | 606/65 |
| 5,531,746 A | 7/1996 | Errico et al. | |
| 5,542,946 A | 8/1996 | Logroscino et al. | |
| 5,545,164 A * | 8/1996 | Howland | 606/250 |
| 5,558,674 A | 9/1996 | Heggeness et al. | |
| 5,616,144 A | 4/1997 | Yapp et al. | |
| 6,017,345 A * | 1/2000 | Richelsoph | 606/70 |
| 6,146,382 A * | 11/2000 | Hurlbert | 606/286 |
| 6,158,437 A * | 12/2000 | Vagley | 128/898 |
| 6,280,442 B1 | 8/2001 | Barker et al. | |
| 6,312,258 B1 * | 11/2001 | Ashman | 433/172 |
| 6,368,321 B1 | 4/2002 | Jackson | |
| 6,485,491 B1 | 11/2002 | Farris et al. | |
| 6,540,748 B2 | 4/2003 | Lombardo | |
| 6,716,214 B1 | 4/2004 | Jackson | |
| 6,893,444 B2 | 5/2005 | Orbay | |
| 6,964,666 B2 | 11/2005 | Jackson | |
| 7,077,843 B2 | 7/2006 | Thramann et al. | |
| 7,141,051 B2 | 11/2006 | Janowski et al. | |
| 7,144,396 B2 | 12/2006 | Shluzas | |
| 2002/0120268 A1 * | 8/2002 | Berger | 606/61 |
| 2002/0143328 A1 * | 10/2002 | Shluzas et al. | 606/61 |
| 2007/0123872 A1 | 5/2007 | Brockmeyer et al. | |

* cited by examiner

*Primary Examiner* — Eduardo C Robert
*Assistant Examiner* — Julianna N Harvey
(74) *Attorney, Agent, or Firm* — Ballard Spahr LLP

(57) ABSTRACT

Methods, systems, and kits for occipital-cervical spinal fixation are provided. A plate configured for attachment to the occipital bone has two arms extending out from either side, which turn downwards parallel to one another. A first bend is disposed in the arms, such that the arms extend down from the occipital bone behind the spinous process of the C1 and C2 vertebrae, upon installation. A second bend in the arms allows attachment to the C2 vertebra. The system may be dimensioned for pediatric installation. A bone graft material may be held in place between the cervical vertebrae and the skull by installing a cable to the installed system to retain the bone graft material in place.

20 Claims, 6 Drawing Sheets

OCCIPITOCERVICAL PLATE

CROSS-REFERENCE TO RELATED APPLICATION

Claim of Priority: Pursuant to the provisions of 35 U.S.C. §119(e), this application claims the benefit of the filing date of provisional patent application Ser. No. 60/574,282, filed May 25, 2004, for "OCCIPITOCERVICAL PLATE," the contents of which are incorporated by reference herein.

FIELD OF THE INVENTION

The present invention relates generally to apparatus and methods for spinal fixation. More specifically, the present invention relates to apparatus and methods for providing internal support and spinal fixation for patients suffering from occipital-cervical instability.

BACKGROUND

Spinal fixation is a well known and frequently used medical procedure. Pedicle, lateral, and oblique mounting devices may be used to secure corrective spinal instrumentation to a portion of the spine that has been selected to be fused by arthrodesis. Fixation of the skull to the cervical spine may be used to treat trauma to the neck, degenerative diseases such as rheumatoid arthritis, and congenital instability. Many current implantable devices designed to immobilize the skull with respect to the upper cervical spine are assemblies of several components which are not designed specifically for fusing the cervical spine to the skull, but instead are assembled from multiple components designed for other applications. Such assembly may prolong and complicate the implantation procedure.

A typical spinal fixation system includes corrective spinal instrumentation that is attached to selected vertebrae of the spine by screws, hooks, and clamps. Various types of screws, hooks, and clamps have been used for attaching such corrective spinal instrumentation to selected portions of a patient's spine. Examples of pedicle screws and other types of attachments are illustrated in U.S. Pat. Nos. 4,763,644; 4,805,602; 4,887,596; 4,950,269; and 5,129,388. Each of these patents is incorporated by reference as if fully set forth herein. Examples of such multipart spinal fixation systems include U.S. Pat. Nos. 5,360,429 and 5,542,946, the disclosure of each of which is incorporated by reference.

With respect to occipital-to-cervical spinal fixation systems, contoured loop and wire constructs, rod constructs, rod and plate constructs and pre-contoured "U-loop"-type constructs have been used. An example of such a device is the OMI "U loop" device manufactured by Ohio Medical Instruments. However, such devices have a number of limitations, including the lack of appropriately sized loops for children under five years of age; the extensive modification and bending of the loops required during surgery, which can lead to failure of the device even before installation; cumbersome methods of coupling the devices to the anchor screws; and the lack of an option for installing a posterior cervical screw, which can be an urgent need for patients with missing lamina or inadequate laminar bone quality.

With these multi-piece systems, a number of problems may occur. For example, pressure necrosis may occur at the points of hook or wire fixation, leading to failure. Supplementation of such systems with halo vests often then fails to prevent micro-motion leading to non-union of the arthrodesis. Additionally, the time for surgery may be extended by the need to build and install a multi-piece assembly from separate components.

A few occipital-cervical spinal fixation systems, such as that disclosed in U.S. Pat. No. 6,146,382, the disclosure of which is incorporated by reference herein, attempt to simplify the implantation of the system by reducing the number of parts. A single plate attaches to an attachment site on the skull, and arms extend down from the plate to the cervical vertebrae. The arms are coplanar with the plate and bend at the tips where a separate connection member is attached. The separate attachment member is then attached at the top surface of the C2 vertebra. A cable is then attached by a hook system to the plate to a vertebra posterior to the arms, in order to retain a bone graft material in place. The '382 device thus still includes a number of parts that are assembled in situ, retaining the issues described with multi-piece systems.

Approximately 500 surgical cases of pediatric occipito-cervical fusions are performed in North America each year on children suffering from occipital-cervical instability. Current occipital-cervical fixation devices, such as the '382 device, are designed for adults and are therefore typically too large for use in children. Additionally, as the relationship of a child's head to the body differs from that of an adult due to allometric growth, devices designed for adults may not sustain the correct relationship of the head and neck for children. Surgical concerns are magnified when treating children, due to their smaller physical size, the abnormal anatomy that may be caused by craniovertebral anomalies, and their growth potential.

Previously, graft/wire constructs were reported to be associated with a nonunion rate as high as 30% for C1-C2 fusion; however, this incidence improves considerably with the use of a halo orthosis. Transarticular screw placement creates immediate atlantoaxial joint stability and, in contrast to previous posterior wiring/graft constructs, does not require post-surgical brace therapy. However, such procedures require surgical precision because serious potential risks are associated with improper screw placement. Thus, many spine surgeons are reluctant to perform such a procedure.

Accordingly, an occipital-cervical spinal fixation system that operated as a single plate, not requiring the use of additional component plates, hooks or rods would be an improvement in the art. Such a system that is configured for use in children or small adults would be an additional improvement in the art.

SUMMARY OF THE INVENTION

One aspect of the present invention relates to occipital-cervical spinal fixation systems. In some embodiments the system includes a plate configured for attachment to the occipital bone, with two arms that extend out from either side of the plate, with the distal end of the arms turning downwards parallel to one another. A bend is placed in the arms, such that the arms extend down from the occipital bone upon installation, behind the spinous process of the C1 and C2 vertebrae. A second bend is placed in the arms, allowing attachment to the C2 vertebrae. Some embodiments are configured in appropriate dimensions for installation in a child for pediatric applications.

Other aspects of the present invention include methods of spinal fixation of the C1 and C2 vertebrae to the occiput. A one-piece spinal fixation system is attached to the C2 vertebra with transarticular screws that extend through the C2 vertebra into the C1 vertebra. The system extends from the occipital bone, behind the spinous process of the C1 and C2 vertebrae.

The transarticular screws may be headless screws requiring only a single emplacement. The system is attached to the occipital bone by one or more attachment screws extending through a top plate. A bone graft material may be held in place between the cervical vertebrae and the skull by installing a cable to the installed system to retain the bone graft material in place.

BRIEF DESCRIPTION OF THE DRAWINGS

While the specification concludes with claims particularly pointing out and distinctly claiming that which is regarded as the present invention, the advantages of this invention and the best mode can be more readily ascertained from the following detailed description when read in conjunction with the accompanying drawings in which:

DETAILED DESCRIPTION

Figure 1:
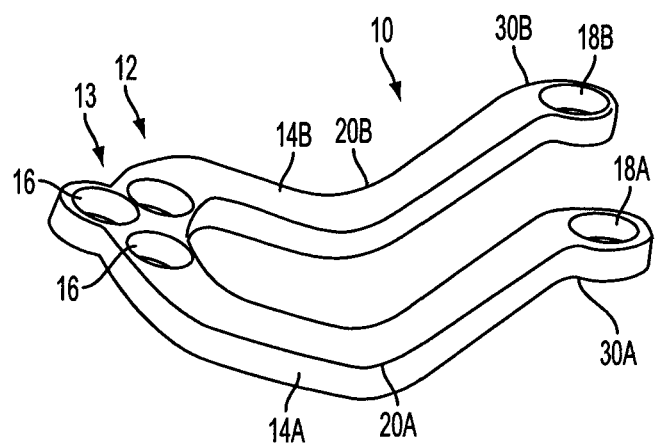
FIG. 1 is a side perspective view of an occipital-cervical fixation system, in accordance with the present invention.
Figure 2:
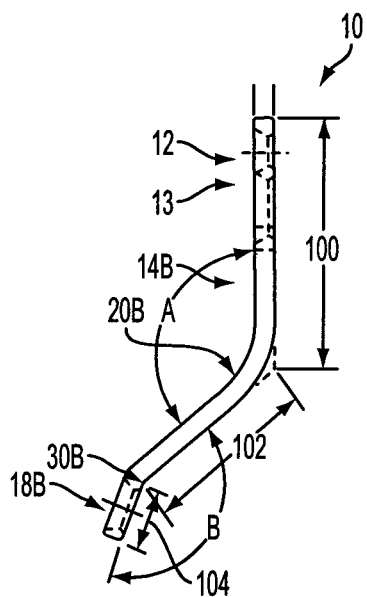
FIG. 2 is a back view of the embodiment of FIG. 1.
Figure 3:
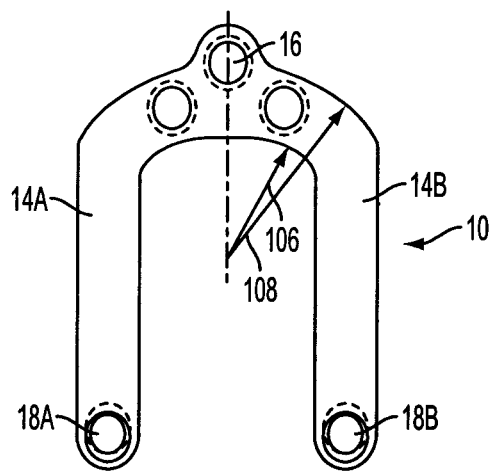
FIG. 3 is a side view of the embodiment of FIGS. 1 and 2.

FIGS. 1, 2 and 3 depict an illustrative embodiment of an occipital-cervical spinal fixation system 10. An attachment plate 12 may be configured for attachment to the occipital bone. Attachment plate 12 may include an enlarged area 13, with one or more attachment holes 16, through which attachment screws 160 (FIG. 6) may be placed to attach the plate to the occipital bone. Each of attachment holes 16 may include beveled edges, allowing an attachment screw placed therein to lie flush with the plate surface (by being countersunk therein). As depicted, the plate 12 may be planar in conformation. The plate 12 may be contoured as desired to fit the surface of the occiput prior to installation.

At opposite sides of plate 12, two arms 14A and 14B extend out from the plate 12 in opposite directions. Each arm 14 then extends downwards becoming generally parallel to one another and generally sharing a common plane throughout their length. It will be appreciated that while the arms 14 may be generally parallels, some variation for individual patients may be required, based on the patients anatomy. Viewed from the front or back (as in FIG. 2), the relationship of the plate 12 and arms 14A and 14B may generally resemble a horseshoe.

Figure 8:
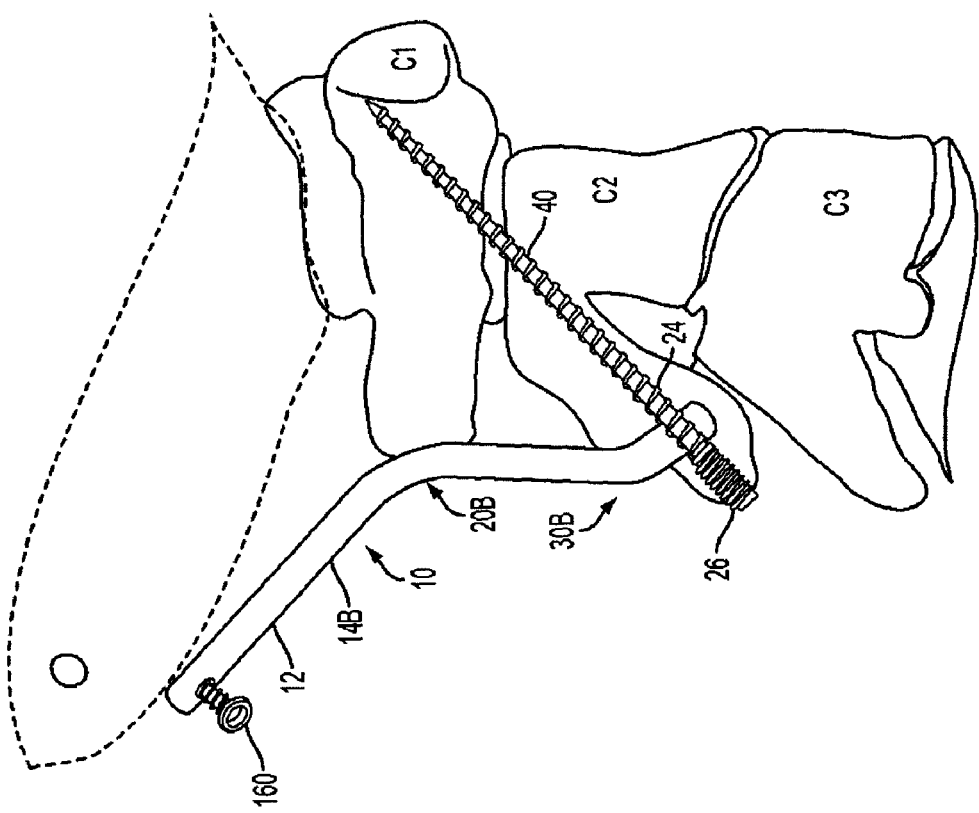
FIG. 8 is a side view of the embodiment of FIGS. 1 to 3, shown in situ in a patient.
Figure 7:
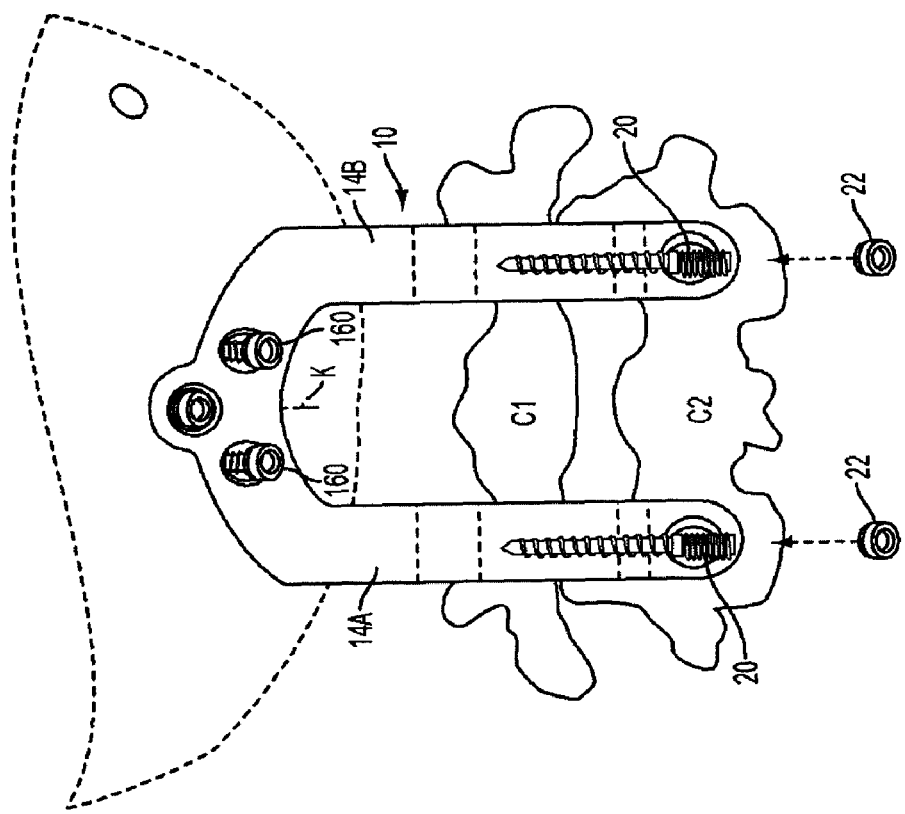

Each arm 14A or 14B contains a bend 20A or 20B in the length thereof, at a distance from the plate. The bends 20A and 20B are generally parallel to one another in the respective arms 14A and 14B, such that the arms 14A and 14B remain generally parallel. Again, it will be appreciated that while the bends 20A and 20B may be generally parallel to each other and arms 14A and 14B may be generally parallel to each other, some variation for individual patients may be required, based on the patient's anatomy. The angle A of bends 20A and 20B is selected to ensure that, upon installation, the arms 14A and 14B extend down from the occipital bone, behind the spinous process of the C1 and C2 vertebrae (as best depicted in FIG. 8). In one embodiment, an angle of about 115 to about 135 degrees, as depicted in FIG. 3 as about 127 degrees, may be used. It will be appreciated that other angles may be used based upon the anatomy of the individual patient.

A second bend 30A and 30B may be placed in each arm, 14A and 14B, respectively, at a point distal to the first bend 20A or 20B. The second bend 30A or 30B positions a distal end of each respective arm such that it may be attached to the lower surface of the spinous process of the C2 vertebrae (as best depicted in FIG. 8). In one embodiment, the angle B of the second bend 30A or 30B may be from about 140 to about 160 degrees, as depicted in FIG. 2 as about 151 degrees, although it will be appreciated that other angles may be used, based upon the anatomy of the patient. Attachment may be accomplished by insertion of a fastener, such as bone screw 20 (FIG. 6) through a fastener hole 18A or 18B located near the distal end of the arm 14. Fastener hole 18A or 18B may include beveled edges, allowing a screw placed therein to lie flush with the plate surface (by being countersunk therein). Long screws 40 that extend through both the C1 and C2 vertebrae may be used, where desirable for the procedure.

Figure 4A:
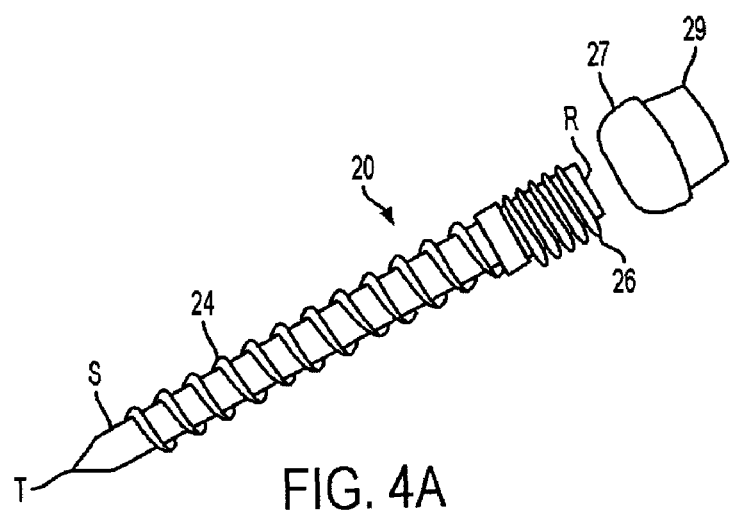
FIG. 4A is an exploded perspective view of bone screw and a retaining nut, useful with the system of FIGS. 1 to 3.
Figure 4B:
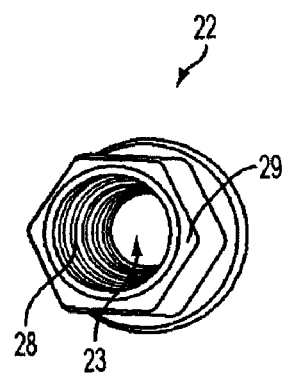
FIG. 4B is a perspective view of the retaining nut of FIG. 4A.
Figure 4C:
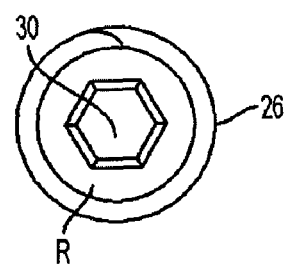
FIG. 4C is a top view of the bone screw of FIG. 4A.

A headless bone screw 20, together with a retaining nut 22, depicted in FIGS. 4A, 4B and 4C, may be used to attach system 10 to the lower surface of the spinous process of the C2 vertebrae. Headless bone screw 20 includes an elongated shaft S, extending from a distal tip T, which may be configured for penetrating bone, to a retaining end R. Bone threads 24 are disposed around the shaft S, extending from near the distal tip T back along the shaft S allowing for secure rotational placement of the bone screw 20 into bone, such as the C1 and C2 vertebrae. It will be appreciated that the depicted bone threads 24 are illustrative only and any spacing and size of thread sufficient to retain the bone screw 20 in place may be used. Retention threads 26 are located on the shaft S near retaining end R, and are configured to rotatably connect with threads 28 disposed on the internal channel 23 of the retaining nut 22. Retention threads 26 are typically smaller in size and more closely spaced than bone threads 24. However, it will be appreciated that the depicted retention threads 26 are illustrative only and any spacing and size of thread sufficient to retain a fastener to the bone screw 20 may be used. A non-threaded area of shaft S, which may be the thickness of the threads 24 or 26, may be disposed between the two sets of threads.

Retaining end R includes structures allowing headless bone screw 20 to be rotatably inserted into bone. As depicted in FIG. 4C, a socket 30 may be formed in retaining end R, into which a tool can be inserted to rotate the headless bone screw 20 by interaction with the sides thereof. It will be appreciated that, although depicted in FIG. 4C as hexagonal, socket 30 may have any desired shape that allows a tool to be inserted therein, examples include square, triangular, irregular, and radially patterned sockets for customized tools. It will also be appreciated that non-socket tool interconnection structures may be used, such as one or more slots for a screwdriver tip disposed on the retaining end R or within a shallow recess disposed thereon.

As depicted, retaining nut 22 has a rounded lower surface 27 for interacting with system 10, and an upper end 29 configured for attachment to a connection tool, such as a wrench. As depicted, upper end 29 is hexagonal shaped, although any desired shape that allows a tool to be removably attached thereto may be used, such as, for example square, triangular, irregular, and radially patterned upper ends for interacting with customized tools.

Fixation system 10 may be configured in dimension for installation in a child. Such configuring may account for both the smaller size of a child's head and neck, as compared to an adult, and for the different allometric relationship of the head to the neck in a child. For example, in one illustrative embodiment, the length from the top of plate 12 to the first set of bends 20A and 20B, depicted by line 100 (FIG. 3.) and including the plate and the upper section of arms 14A and 14B may be around 32 mm. A second length between the two bends 20A and 20B and 30A and 30B, as represented by line 102 (FIG. 3) may be around 22 mm. A third length between the second bend 30A or 30B and the distal end of the respective arms 14A and 14B may be around 6 mm as depicted by line 104. A ratio of 16:11:3 may thus be realized. It will be appreciated that different lengths may be used for each of these features, depending on the age and anatomy of the patient. Accordingly, different ratios may be used for children at different stages of development.

Table I below provides some illustrative examples of measurements (in millimeters) that may be used on some embodiments in accordance with the principles of the present invention.

| Embodiment | 1 | 2 | 3 | 4 | 5 | 6 | 7 | 8 |
|---|---|---|---|---|---|---|---|---|
| Plate thickness | 3 | 3 | 3 | 3 | 3 | 3 | 3 | 3 |
| Coronal Width | 26 | 28 | 30 | 32 | 34 | 36 | 38 | 40 |
| Distance Bend A to Bend B | 18 | 20 | 22 | 24 | 26 | 28 | 30 | 34 |
| Distance Bend B to Coronal tip (generally variable between 30 and 36, dependent on patient need) | 30.4 | 31.2 | 32 | 32.8 | 33.6 | 34.4 | 35.2 | 36 |
| Plate width | 7 | 7 | 7 | 7 | 7 | 7 | 7 | 7 |
| Accepts Screw Size | 3.5 | 3.5 | 3.5 | 3.5 | 3.5 | 4 | 4 | 4 |

In such embodiments, tab length may be between 6 and 10, plate thickness may be around 7 and arm width may be around 8.6. All measurements are given in mm and are merely illustrative. Embodiments have different measurements are contemplated within the scope of the present invention. For example, larger embodiments of a system may be constructed for use in adult patients. For smaller adult patients or patients with anatomical variations, different embodiments may be constructed having different dimensions as appropriate for the patient.

The curve of the arms 14 when extending from plate 12 may also be expressed as a ratio. As depicted in FIG. 3, the inside curve of the bend may have a radius of approximately 12.5 mm (as depicted by arrow 106), while the outer curve may have a radius of about 22 mm (as depicted by arrow 108), giving a ratio of 12.5:22. Each arm 14 may have a width of around 7.8 mm and be spaced apart from each other in a common plane by about 30 mm measured from a centerline axis of each arm 14. In such a sized embodiment, the system may have a thickness of around 2 mm and the edges of the system may be rounded to about 1 mm. Again, it will be appreciated that these measurements are for one merely illustrative pediatric embodiment and that embodiments having different measurements are contemplated within the scope of the present invention. For example, larger embodiments of a system may be constructed for use in adult patients, which could maintain a similar ratio for these curves.

Once being made aware of the system 10, those of ordinary skill in the art will be readily able to make the components thereof with the use of conventional materials. For example, the plate 12 may be formed from any suitable biocompatible material, including metal, such as titanium, stainless steel, cobalt-chromium-molybdenum alloys, titanium-aluminum vanadium alloys, other metals and alloys, or even a biocompatible plastic, such as an ultra high molecular weight polyethylene. Arms 14A and 14B may be constructed from similar suitable materials. It will also be appreciated that bone screws 20, retaining nuts 22 and attachment screws 160 may be constructed of similar materials.

Figure 9:
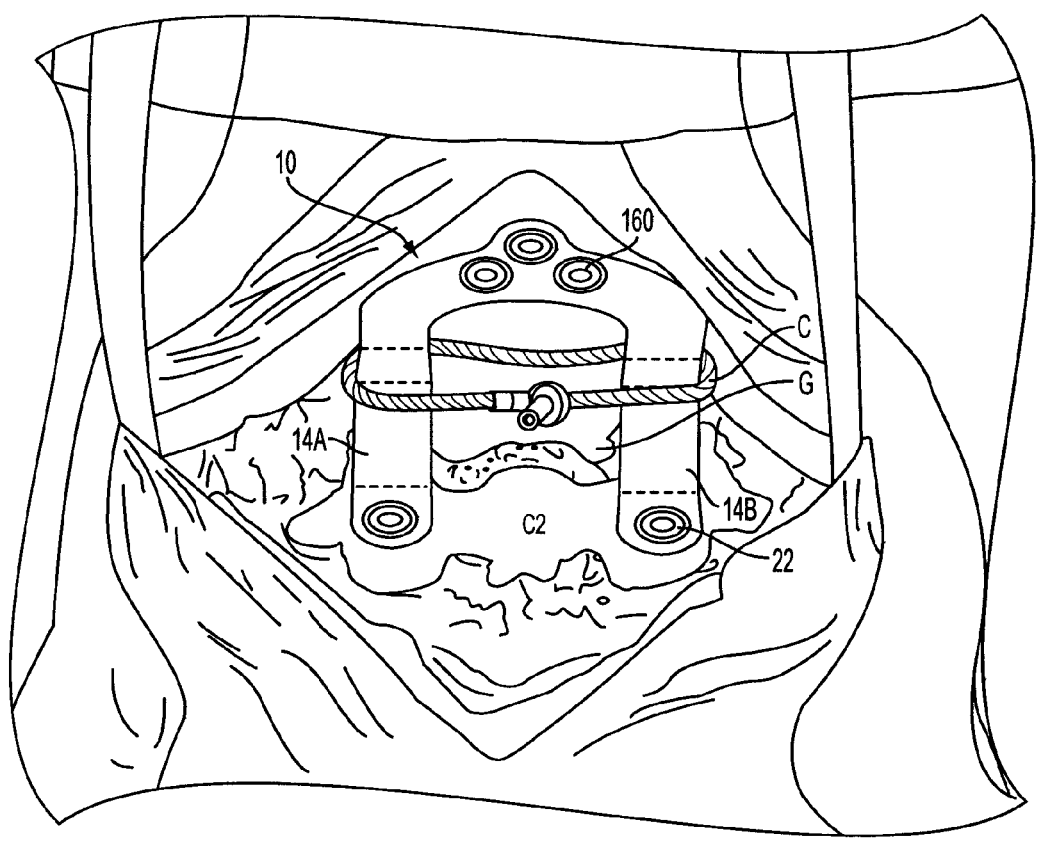
FIG. 9 is a back view of the embodiment of FIGS. 1 to 3, shown in situ in a patient, in conjunction with a bone graft material.

FIGS. 5 through 9 show the installation and use of one embodiment of a system 10. As best depicted in FIG. 9, upon the completion of installation, the plate 12 is fastened to the occiput O with at least one attachment bone screw 160 passing through one of the attachment holes 16. Where desirable, multiple attachment bone screws 160 may be used in the different attachment holes 16. Where possible, it may be desirable that at least one bone screw 160 be placed into the midline keel of the occiput O. Multiple attachment holes 16 may allow such placement with minimal adaptation of the system 10. A transarticular headless bone screw 20 passes through fastener hole 18 in each arm 14 and into both the C2 and C1 vertebrae, attaching the system 10 thereto in conjunction with the retention nut 22 rotatably retained thereon. It will be appreciated that a bone screw having a head, rather than a headless bone screw 20 may be used in conjunction with system 10, as will be explained further herein.

Figure 6:
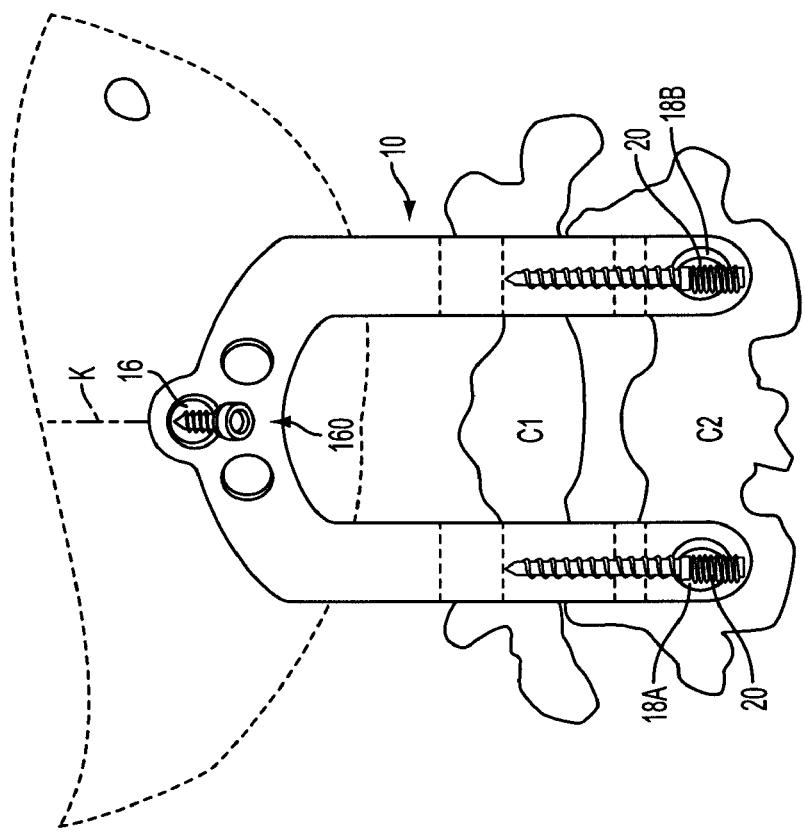
FIGS. 6 and 7 are back views of the embodiment of FIGS. 1 to 3, shown in situ in a patient.
Figure 5:
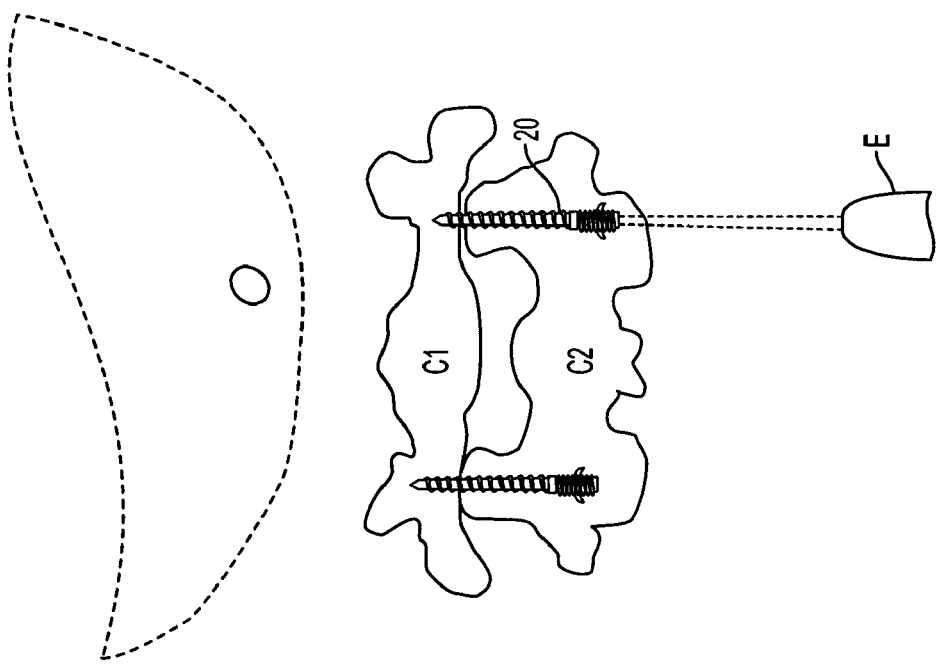
FIG. 5 is a back view of emplacement of the bone screw of FIG. 4A in a patient, in accordance with the present invention.
Figure 11A:
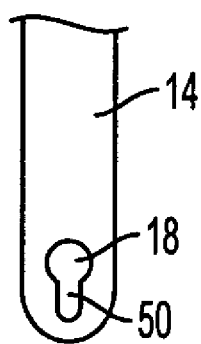
FIGS. 11A and 11B are back views of alternate embodiments of lower attachment holes for embodiments of occipital-cervical fixation systems in accordance with the present invention.

Typically, prior to installation, a detailed image of the patient's occipital-cervical region is performed, such as a thin-cut CT scan or other appropriate imaging technique, to allow selection of an appropriate system 10 and guidance through the procedure. The placement of the system 10, and the attachment screws may be performed under intraoperative fluoroscopy. For placement, the system 10 may be placed in position, the attachment and fastener hole positions marked. The system 10 may then be removed and the attachment sites prepared for insertion of bone screws, which may involve placement or partial emplacement thereof. As depicted in FIG. 5, bone screws, such as headless screws 20 may be placed transarticularly passing angularly upwards through the C2 vertebra into the C1 vertebra (as depicted in FIG. 8) using an emplacement tool E. Where appropriate, paths for the insertion of the bone screws may be drilled prior to insertion. Where headless bone screws 20 are used, the screws may then be left in place and the system 10 mounted with the retention end R of each screw protruding through an attachment hole 18A or 18B, as depicted in FIG. 6. Where headed bone screws are used, the screws may be entirely or partially emplaced, then removed, the plate positioned and the screws re-emplaced to attach the system 10. In some embodiments, fastener hole 18 may have a keyhole 50 extension that allows the system to be emplaced around a partially inserted transarticular screw, as shown in FIG. 11A. Fastener hole 18 may also be formed as a recessed slot 52 (FIG. 11B) allowing for adjustment of the system during emplacement, following insertion of the transarticular bone screws.

Attachment is completed by the attachment of the plate 12 the occiput O with at least one attachment bone screw 160 passing through one of the attachment holes 16. Multiple attachment bone screws 160 may be used in the different attachment holes 16. Where possible, at least one bone screw 160 may be placed into the midline keel K of the occiput O. Multiple attachment holes 16 may allow such placement with minimal adaptation of the system 10. Where appropriate, paths for the insertion of the bone screws may be drilled prior to insertion.

A bone graft material G, such as iliac crest or rib, (FIG. 9) may be placed between the occiput O and the vertebrae to promote fusion therebetween. The system 10 retains the bone graft material G in proper position and under compression to facilitate fusion between the occiput and the vertebrae, using a cable C, which is wrapped around the system 10 to retain the bone graft B in place. From the foregoing discussion, it will be apparent that use of a system or method in accordance with the present invention may lead to short surgery times and stronger systems than current procedures.

It will be appreciated that systems and methods of the present invention may be used to treat craniocervical junction instability through fusion of the occiput-C2 region, where the instability results from any cause, so long as patient's is sufficiently healthy to undergo implantation surgery and the patient's anatomy will allow successful implantation. Examples of causes of such instability that may be treated with the systems and methods of the present invention include trauma, os odontoideum, congenital anomaly (such as Down syndrome, Stihl disease, metatrophic dwarf, Morquio syndrome, Klippel-Feil syndrome, axis assimilation, or skeletal dysplasia), neoplasm, rheumatoid arthritis, or chronic instability.

Figure 10:
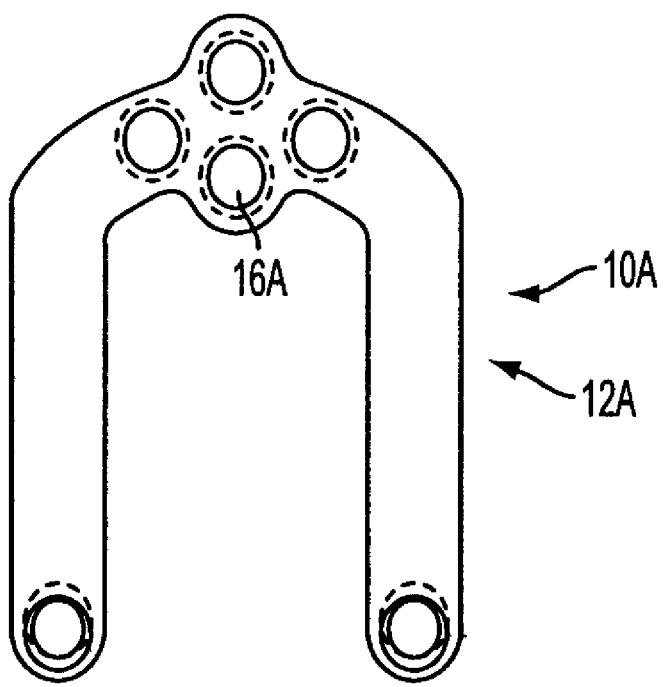
FIG. 10 is a back view of a second embodiment of an occipital-cervical fixation system, in accordance with the present invention.

FIG. 10 depicts a back view of another embodiment of a system 10A in accordance with the teachings of the present invention. Similar to system 10, system 10A differs by having an enlarged plate 12A with an additional attachment hole 16A, that extends down between the arms 14 of the system. Such a system 110A may facilitate placement attachment bone screw 160.

Figure 11B:
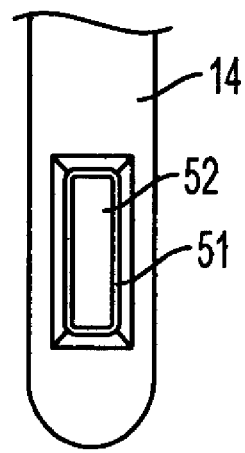

FIGS. 11A and 11B depict alternative embodiments of fastener holes 18. For example, fastener hole 18 may have a keyhole 50 extension that allows the system to be emplaced around a partially inserted transarticular screw having a head, as shown in FIG. 11A. Fastener hole 18 may also be formed as a recessed slot 52 (FIG. 11B) with a shelf 51 therein allowing for adjustment of the system during emplacement, following insertion of the transarticular bone screws.

In order to facilitate use of a spinal fixation system in accordance with the present invention, a kit is included within the scope of the present invention. Such a kit may include a system in accordance with the present invention (such as a system 10 or 10A), transarticular screws or headless bone screws 20 and retaining nuts 22, attachment bone screws 160, drill guides, cable (such as a titanium cable), taps and calipers, all sized appropriately for use together. Such a kit may be provided in sterile form in a sealed sterile container. Individual kits may be selected based on the size of the system 10 or 10A appropriate for the intended usage.

EXAMPLES

Data used in this example was also used in preparing the paper, Gluf and Brockmeyer, Atlantoaxial transarticular screw fixation: a review of surgical indications, fusion rate, complications, and lessons learned in 67 pediatric patients, J. Neurosurg Spine 2:164-169, 2005, the disclosure of which is incorporated herein by reference.

23 pediatric patients were treated for occipital cervical instability by occipitocervical fusion performed with implants in conjunction with C1-C2 transarticular screws. While older patients were treated using Ohio Medical Instruments U-loop, rod/plate devices, patients from the ages of 2 to 5 years of age were treated using a system in accordance with the present invention, referred to as the Avery Brockmeyer-Thiokol plate, sized to fit patients 2 to 5 years of age.

A preoperative imaging protocol including plain cervical flexion-extension radiography and thin-cut (1-mm) CT scanning of the occiput-C3 region with sagittal and coronal reconstructions was performed. However, no presurgical flexion-extension x-ray films were obtained in traumatically injured patients with obviously unstable atlantoaxial or craniovertebral fractures. Craniovertebral magnetic resonance imaging was found to be helpful in some cases but not critical in the planning phase for placing C1-C2 transarticular screws. Image analysis of the thin-cut CT scan was performed on a high-speed CT workstation with multiplanar reconstructions in the screw trajectory pathway being generated to determine the best path for screw placement.

In general, 3.5-mm-outer-diameter screws were used for transarticular placement in patients 4 years of age and younger and 4-mm-outer-diameter screws for patients older than the age of 4 years. However, as each case is individualized, however, appropriate screw diameter for each patient was determined only after careful study of the reformatted CT scans.

Before surgery, an understanding of the anatomical landmarks for determining the starting point for screw trajectory was obtained. The screw starting point is measured in millimeters from the midportion of the C2-C3 facet joint and the screw trajectory is defined in number of degrees from both the parasagittal plane and the dorsal or ventral position of the screw relative to the VA foramen in C-2. Where a patient's anatomy was unsuitable for using C1-C2 transarticular screws on either side, a pars screw was placed, which was found to be usually sufficient to anchor the chosen type of occipitocervical hardware.

Once the patient was intubated (either with axial traction or with a hard collar in place), he or she was lifted and turned carefully into the prone position. Mayfield three-point fixation was routinely used in all patients, even those as young as 2 years of age. Gentle axial traction was applied (except in cases of occipitoatlantal dislocation) under direct lateral fluoroscopic vision and the patient's neck flexed and posteriorly translated into the so-called military tuck position. During occipitocervical fusion, the patients were realigned into a neutral position prior to placing the rigid occipito cervical instrumentation to avoid the problem of fusion occurring in a nonanatomical flexed position.

Postoperative imaging demonstrated successful fusion in all patients. Postoperative imaging included plain radiographs obtained at 1 and 2 months and fine-cut CT scans of the occiput-C3 region reconstructed two dimensionally 4 months after surgery. If solid fusion was not evident on the 4-month CT reconstruction, monthly repeated CT scanning involving the same protocol used in the 4-month study was performed until confirmation of fusion. Fusion was defined as continuous, bridging trabecular bone seen between the occiput and C-2 on two-dimensional sagittal reconstructions of thin-cut CT scans indicated fusion.

It will be apparent that details of the apparatus, processes, and methods herein described can be varied considerably without departing from the concept and scope of the invention.

What is claimed is:

1. An occipital-cervical spinal fixation system for a patient, comprising:
   a monolithic plate having an anterior surface and a posterior surface, the plate comprising:
      a central portion defining at least one transversely extending central bore, wherein the at least one central bore extends along a longitudinal axis between the anterior and posterior surfaces, wherein at least a portion of the anterior surface of the central portion is configured to contact a portion of an occipital bone of the patient, and wherein the central portion of the plate is in a first plane;
      a first arm, wherein at least a portion of the first arm extends away from the central portion substantially parallel to the central portion before extending downwardly and away from the central portion, wherein the first arm defines a first arm bore near a distal end of the first arm, wherein the first arm bore extends along a longitudinal axis between the anterior and posterior surface, wherein the distal end of the first arm is in a second plane that is at a first acute angle relative to the first plane, wherein at least a portion of the first arm that extends downwardly and away from the central portion is in a third plane, and wherein the third plane is positioned at an acute angle relative to the first plane and the second plane; and
      a second arm, wherein at least a portion of the second arm extends away from the central portion substantially parallel to the central portion before extending downwardly and away from the central portion, wherein the second arm defines a second arm bore near a distal end of the second arm, wherein the second arm bore extends along a longitudinal axis between the anterior and posterior surface, wherein the distal end of the second arm is substantially in the second plane, and wherein at least a portion of the second arm that extends downwardly and away from the central portion is substantially in the third plane,
      wherein at least a portion of the anterior surface of the distal end of the respective first and second arm is configured to contact a portion of a vertebra of the patient.

2. The system of claim 1, wherein the first arm bore and the second arm bore comprise a bevelled edge for interaction with a fastener.

3. The system of claim 1, wherein the first arm bore comprises a substantially round cross-sectional shape.

4. The system of claim 1, wherein the second arm bore comprises a substantially round cross-sectional shape.

5. The system of claim 1, wherein the first arm bore comprises a keyhole-shaped cross-sectional shape.

6. The system of claim 1, wherein the second arm bore comprises a keyhole-shaped cross-sectional shape.

7. The system of claim 1, wherein the distal end of the first arm defines a recessed slot, wherein the recessed slot is bisected by the first arm bore.

8. The system of claim 1, wherein the distal end of the second arm defines a recessed slot, wherein the recessed slot is bisected by the second arm bore.

9. The system of claim 1, further comprising at least one bone screw, wherein the plate is attachable to the occipital bone of the patient by insertion of the at least one bone screw through the at least one central bore defined in the central portion of the plate.

10. The system of claim 1, further comprising at least one bone screw, wherein the plate is attachable to the C2 vertebra of the patient by insertion of the at least one bone screw through at least one of the first arm bore or the second arm bore defined in the plate.

11. The system of claim 1, further comprising at least one headless bone screw.

12. The system of claim 11, further comprising at least one retaining nut for attachment to the at least one headless bone screw.

13. The system of claim 11, wherein the at least one headless bone screw comprises retention threads on a proximal end of the at least one headless bone screw.

14. The system of claim 11, wherein the headless bone screw comprises an interconnect structure.

15. The system of claim 1, wherein the plate is formed of a material from the group consisting of titanium, stainless steel, a cobalt-chromium molybdenum alloy, a titanium-aluminum vanadium alloys, or a biocompatible plastic.

16. The system of claim 1, wherein an angle formed between the longitudinal axis of the first arm bore and the longitudinal axis of the at least one central bore is substantially equal to the first acute angle.

17. A kit for performing an occipital-cervical fusion of a patient, the kit comprising:
   at least one attachment bone screw; and
   a monolithic plate having an anterior surface and a posterior surface, the plate comprising:
      a central portion defining at least one transversely extending central bore, wherein the at least one central bore extends along a longitudinal axis between the anterior and posterior surfaces, wherein at least a portion of the anterior surface of the central portion is configured to contact a portion of an occipital bone of the patient, and wherein the central portion of the plate is in a first plane,
      a pair of opposed arms, wherein at least a distal portion of the opposed arms are positioned substantially parallel to each other, wherein at least a portion of each arm extends away from the central portion substantially in the first plane before extending downwardly and away from the central portion, wherein each arm defines an arm bore near a distal end of each arm, wherein each arm bore extends along a longitudinal axis between the anterior and posterior surface, wherein the distal end of each arm is substantially in a second plane positioned at a first acute angle relative to the first plane, and wherein an intermediate portion of each arm is substantially in a third plane that is positioned at an acute angle relative to the first plane and the second plane,
      wherein at least a portion of the anterior surface of each arm of the pair of opposed arms is configured to contact a portion of a vertebra of the patient.

18. An occipital-cervical spinal fixation system for a patient, comprising:
   a monolithic plate having an anterior surface and a posterior surface, the plate comprising:
      a central portion in a first plane;
      a pair of opposed arms, wherein at least a distal portion of the opposed arms are positioned substantially parallel to each other, wherein at least a portion of each arm extends away from the central portion substantially in the first plane before extending downwardly and away from the central portion, wherein each arm defines an arm bore near a distal end of each arm, wherein each arm bore extends along a longitudinal axis between the anterior and posterior surface, wherein the distal end of each arm is substantially in a second plane positioned at a first acute angle relative to the first plane, and wherein an intermediate portion of each arm is substantially in a third plane that is positioned at an acute angle relative to the first plane and the second plane;

means for attaching at least a portion of the anterior surface of the central portion of the plate to the occipital bone of the patient; and means for attaching at least a portion of the anterior surface of each arm of the pair of opposed arms to a vertebra of the patient.

19. The system of claim 18, wherein the means for attaching at least a portion of the anterior surface of the central portion of the plate to the occipital bone comprises bone screw insertable through at least one central bore in the central portion and securable to the occipital bone, and the means for attaching at least a portion of the anterior surface of each arm of the pair of opposed arms to a vertebra comprises a bone screw insertable through each arm bore and securable to the vertebra.

20. The system of claim 18, wherein the at least one of the means for attaching comprises a headless bone screw.

* * * * *